(12) United States Patent
Büchs et al.

(10) Patent No.: US 11,635,381 B2
(45) Date of Patent: Apr. 25, 2023

(54) METHOD AND DEVICE FOR MEASURING PROCESS PARAMETERS IN LIQUID CULTURES

(71) Applicant: RHEINISCH-WESTFÄLISCHE TECHNISCHE HOCHSCHULE (RWTH) AACHEN, Aachen (DE)

(72) Inventors: Jochen Büchs, Aachen (DE); Tobias Ladner, Aachen (DE); Georg Wandrey, Aachen (DE); Oliver Paquet-Durand, Stuttgart (DE); Bernd Hitzmann, Stuttgart (DE)

(73) Assignee: RHEINISCH-WESTFÄLISCH TECHNISCHE HOCHSCHULE (RWTH) AACHEN, Aachen (DE)

( * ) Notice: Subject to any disclaimer, the term of this patent is extended or adjusted under 35 U.S.C. 154(b) by 1038 days.

(21) Appl. No.: 16/329,364

(22) PCT Filed: Aug. 16, 2017

(86) PCT No.: PCT/EP2017/070774
§ 371 (c)(1),
(2) Date: Feb. 28, 2019

(87) PCT Pub. No.: WO2018/041634
PCT Pub. Date: Mar. 8, 2018

(65) Prior Publication Data
US 2019/0219508 A1  Jul. 18, 2019

(30) Foreign Application Priority Data
Sep. 1, 2016 (DE) .................. 10 2016 116 377.5

(51) Int. Cl.
*G01N 21/64* (2006.01)
*C12M 3/06* (2006.01)
(Continued)

(52) U.S. Cl.
CPC ......... *G01N 21/6452* (2013.01); *C12M 27/16* (2013.01); *C12M 41/46* (2013.01);
(Continued)

(58) Field of Classification Search
CPC .. G01N 21/6452; G01N 1/286; G01N 21/253; G01N 2021/6419;
(Continued)

(56) References Cited

U.S. PATENT DOCUMENTS 4,349,510 A * 9/1982 Kolehmainen .. G01N 35/00009
435/808
5,595,708 A 1/1997 Berndt
(Continued)

FOREIGN PATENT DOCUMENTS

CN  1938576 A  3/2007
CN  101236153 A  8/2008
(Continued)

OTHER PUBLICATIONS

Perez et al., "Optical Fiber Sensors for Chemical and Biological Measurements", Current Developments in Optical Fiber Technology, 2012 (Year: 2012).*
(Continued)

*Primary Examiner* — Samuel P Siefke
*Assistant Examiner* — Henry H Nguyen
(74) *Attorney, Agent, or Firm* — Lucas & Mercanti, LLP

(57) ABSTRACT

A method for measuring process parameters in liquid cultures in a plurality of microreactors of at least one microtiter plate includes continuously agitating the liquid cultures using an orbital agitator at least until the reaction is completed in all the microreactors. In order to allow process parameters also of such substances which themselves do not have any fluorescence activity to be measured with relatively low complexity and within a short time, 2D fluores- (Continued)

cence spectra are recorded in a plurality of in particular different liquid cultures in the microreactors of agitated microplates. A device for carrying out the method is also disclosed.

35 Claims, 16 Drawing Sheets

(51) Int. Cl.
*C12M 1/34* (2006.01)
*G01N 21/25* (2006.01)
*G01N 1/28* (2006.01)
*B01F 31/22* (2022.01)
*C12M 3/00* (2006.01)

(52) U.S. Cl.
CPC ............ *G01N 1/286* (2013.01); *G01N 21/253* (2013.01); *B01F 31/22* (2022.01); *C12M 3/00* (2013.01); *G01N 2021/6419* (2013.01); *G01N 2021/6421* (2013.01); *G01N 2201/08* (2013.01); *G01N 2201/1293* (2013.01)

(58) Field of Classification Search
CPC ....... G01N 2021/6421; G01N 2201/08; G01N 2201/1293; C12M 27/16; C12M 41/46; C12M 3/00; B01F 31/22
See application file for complete search history.

(56) References Cited

U.S. PATENT DOCUMENTS

| | | | |
|---|---|---|---|
| 6,673,532 B2 | 1/2004 | Rao | |
| 8,268,632 B2 | 9/2012 | Büchs | |
| 8,828,337 B2 | 9/2014 | Kensy | |
| 2001/0046045 A1 | 11/2001 | Dong | |
| 2004/0115648 A1 | 1/2004 | Eddison | |
| 2004/0106201 A1 | 6/2004 | Blum | |
| 2006/0007439 A1* | 1/2006 | Corcoran | G01J 3/02 356/318 |
| 2007/0256510 A1 | 11/2007 | Buchs | |
| 2009/0116008 A1* | 5/2009 | Fukuda | G02B 21/0076 356/317 |
| 2011/0306087 A1* | 12/2011 | Galiano | G01N 21/51 435/288.7 |

FOREIGN PATENT DOCUMENTS

| | | |
|---|---|---|
| CN | 102253016 A | 11/2011 |
| CN | 103149187 A | 6/2013 |
| DE | 10052511 A1 | 5/2002 |
| DE | 10214517 A1 | 6/2003 |
| DE | 10230320 A1 | 2/2004 |
| DE | 102008008256 A2 | 4/2009 |
| GB | 2254423 A | 10/1992 |
| JP | 2003522578 A | 7/2003 |
| JP | 2007530270 A | 11/2007 |
| JP | 2010185719 A | 8/2010 |
| NL | 2002055 C | 4/2010 |
| WO | 9210754 A1 | 6/1992 |
| WO | 0160247 A1 | 8/2001 |
| WO | 2005098397 A1 | 10/2005 |
| WO | 2010037862 A1 | 4/2010 |

OTHER PUBLICATIONS

Rohe et al., "An automated workflow for enhancing microbial bioprocess optimization on a novel microbioreactor platform", Microbial Cell Factories 2012, 11:144 (Year: 2012).*
Translation of CN103149187A, Zhou, Peng, Jun. 12, 2013 (Year: 2013).*
Faassen et al., "Fluorescence Spectroscopy and Chemometric Modeling for Bioprocess Monitoring", Sensors 2015, 15, 10271-10291 (Year: 2015).*
David A Ullisch: "A Fundamental Research 1-9, of Growth, Metabolism and Product Formation of Tobacco Suspension Cells at Different Scales", Jan. 2, 2012 (Jan. 2, 2012), pp. 1-141.
"FluoroMax-4 & FluoroMax-4P with USB (Auszug)", Operation Manual, Part number J810005 rev. D, Jun. 30, 2012 (Jun. 30, 2012), XP055416166, Retrieved from the Internet: URL:http://www.horiba.com/fileadmin/uploads/Scientific/Downloads/UserArea/Fluorescence/Manuals/FluoroMaxA_4P Manual_USB.pdf [retrieved on Oct. 16, 2017]—the whole document.
Kensy Frank et al: "Scale-up from microtiter plate to laboratory fermenter: evaluation by online monitoring techniques of growth and protein expression in *Escherichia coli* and Hansenula polymorphs fermentations", Microbial Cell Factories, vol. 8, No. 1, Dec. 22, 2009 (Dec. 22, 2009), p. 68.
Stefan Marose et al: "Two-Dimensional Fluorescence Spectroscopy: A New Tool for on-Line Bioprocess Monitoring", Biotechnology PROGR, American Institute of Chemical Engineers, US, vol. 14, No. 1, Jan. 2, 1998 (Jan. 2, 1988), pp. 63-74.
Jong Il Rhee, Application of principal component analysis and self-organizing map tot he analysis of 2D fluorescence spectra and the monitoring of fermentation processes, Biotechnology and Bioprocess Engineering, 2006, vol. 11, pp. 432-441, URL: https://link.springer.com/article/10.1007/BF02932311.
Funke Matthias et al: "Bioprocess Control in Microscale: Scalable Fermentations in Disposable and User-Friendly Microfluidic Systems" Microbial Cell Factories, vol. 9, No. 1, Nov. 13, 2010 (Nov. 13, 2010), p. 86, XP021088165.
M. Samorskl et al: "Quasl-continuous combined scattered light and fluorescence measurments: A novel measurement technique for shaken microtiter plates", Biotechnology and Bioengineering, vol. 92, No. 1, Oct. 5, 2005 (Oct. 5, 2005), pp. 61-68, XP055194633.
English Translatlon of Internatonal Preliminary Report on Patentability; dated Mar. 5, 2019; 10 Pages.
"Modern Physics Experiments", MA Hongliang et al., No.-100, Shanghai University Press, Nov. 30, 2005, 11 Pages.
"Plasma Science and Technology and Its Application in Industry", GE Yuanjing et al., pp. 288-292, China Light Industry Press, Jan. 31, 2011, 9 Pages.
Office Action of the Chinese Patent Office (CNIPO) dated Mar. 18, 2022, 29 Pages.
Decision of Rejection of the Chinese Patent Office dated Aug. 17, 2022, 18 Pages.

* cited by examiner

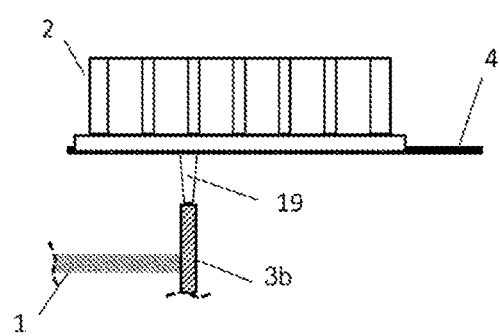
Fig. 4A
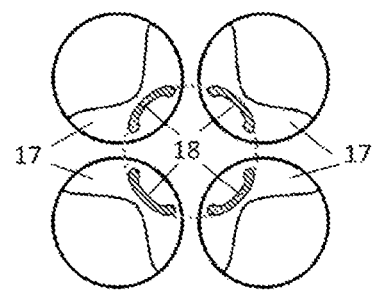
Fig. 4B
Fig. 4C

METHOD AND DEVICE FOR MEASURING PROCESS PARAMETERS IN LIQUID CULTURES

CROSS-REFERENCE TO RELATED APPLICATIONS

This application is a 371 of PCT/EP2017/070774 filed Aug. 16, 2017, which in turn claims the priority of DE 10 2016 116 377.5 filed Sep. 1, 2016, the priority of both applications is hereby claimed and both applications are incorporated herein by reference.

BACKGROUND OF THE INVENTION

The invention relates to a method and a device for measuring process parameters by means of 2D fluorescence spectroscopy in liquid cultures in a plurality of microreactors of at least one microtiter-plate that are continuously agitated using an orbital shaker at least until the reaction is completed in all the microreactors.

A method and devices for measuring process parameters in microbial cultures in a plurality of microreactors of a microtiter plate that are continuously agitated using an orbital shaker at least until the reaction is completed in all the microreactors are known from EP 1730494 B1. The known method is suitable in particular for automated measurement of process parameters of microbial cultures that are continuously agitated until the reaction is completed in all of the microreactors. As process parameters, for example, the fluorescence of fluorescent proteins or amino acids and optical backscattering as a measure of biomass concentration are measured.

The device known from EP 1730494 B1 for carrying out the method has a microreactor platform connected to an orbital shaker, on which a microtiter plate with a transparent bottom is arranged that is continuously subjected to orbital shaking until the reaction is completed in all of the microreactors. Measurement of the process parameters is carried out using an optical sensor element that comprises a photosensitive sensor, a light source and at least one optical waveguide. An end of the optical waveguide is moved from microreactor to microreactor by means of an x-y positioning unit underneath the microtiter plate. The light from a light source is coupled in at the end of the optical waveguide, which is preferably configured to be y-shaped, while a photosensor is arranged on the other strand of the y-shaped optical waveguide. The optical waveguide is not moved during measurement of the process parameters, so that the agitated microreactors move relative to the optical waveguide. The relative movement occurring between the microreactors and the optical waveguide, which is stationary for the measurement, is unproblematic, provided that the electromagnetic radiation is introduced exclusively into one of the microreactors and electromagnetic radiation (emission) emitted by the microreactor as a result of the introduced electromagnetic radiation (excitation light) is measured exclusively by the photosensor of the optical sensor element. The introduced electromagnetic radiation is introduced with a specified excitation wavelength. As a result, in the known methods, it is only possible to measure process parameters of substances that show fluorescence activity with respect to the incoming electromagnetic radiation or backscattering.

BRIEF SUMMARY OF THE INVENTION

Based on this prior art, the object of the invention is to provide a method that also allows measurement of process parameters of substances that themselves have no fluorescence activity. Moreover, the method is intended to allow determination of the physiological state of the liquid culture and substance transfer rates with little complexity and within a short period of time. Finally, a device for carrying out the method is provided.

The achievement of this objects is based on the concept of recording 2D fluorescence spectra in a plurality of in particular different liquid cultures in microreactors of agitated microtiter plates.

More specifically, the object is achieved by means of a method for determining process parameters using 2D fluorescence spectroscopy in liquid cultures using a device having a plurality of microreactors of at least one microtiter plate, the liquid cultures being held in the microreactors, an orbital shaker configured to agitate the liquid cultures by moving the at least one microtiter plate in an agitating motion at least until completion of cultivation in all of the microreactors, and at least one measuring device configured to record 2D fluorescence spectra of the liquid cultures during cultivation, the at least one measuring device being decoupled from the agitating motion of the microtiter plate. The method comprises the following steps:

1.1 producing monochromatic excitation light, the excitation wavelength of which is modified step by step, 1.2 successively introducing the excitation light with different excitation wavelengths into the liquid culture in one of the microreactors, 1.3 guiding emission spectra from the liquid culture in the one of the microreactors to an optical element that decomposes the emission spectrum for each excitation wavelength into the different wavelengths and depicts the emission spectrum fanned out on a sensor matrix with photosensitive sensors, 1.4 recording, using a sensor matrix of the at least one measuring device, a 2D fluorescence spectrum by measuring an intensity of the different wavelengths of each emission spectrum of each excitation wavelength from the liquid culture in the one of the microreactors, and 1.5 using steps 1.1-1.4 to record 2D fluorescence spectra of the liquid cultures in further microreactors of the at least one microtiter plate.

The object is also achieved by a device for measuring process parameters using 2D fluorescence spectroscopy. The device comprises a microreactor platform connected to an orbital shaker on which at least one microtiter plate with a plurality of microreactors is arranged, the microreactors configured to hold liquid cultures and the orbital shaker configured to agitate the liquid cultures by moving the at least one microtiter plate in an agitating motion. The device further includes a light source, an automatically tunable monochromator for spectral isolation of different wavelengths from the incident light of the light source, configured to produce monochromatic excitation light, the excitation wavelength of which is modified step by step, and a beam guidance system comprising an optical coupler that is configured for transferring the excitation light from the monochromator to the liquid culture and for transferring the emission spectrum from the liquid culture to an optical element. The optical coupler for introducing the excitation light into the liquid culture and for coupling the emission spectrum into the beam guidance system on a section of the microreactor is oriented with respect to a section of the microreactor that is permeable to electromagnetic radiation and the optical element decomposes the emission spectrum for each excitation wavelength into the different wavelengths and fans it out. The device further includes a sensor matrix with photosensitive sensors, the optical element depicting the fanned-out emission spectrum on the sensor matrix. The sensor matrix is configured to record a 2D fluorescence spectrum by measuring the intensity of the different wavelengths for each emission spectrum.

Using a conventional fluorescence spectrometer, it takes up to 25 minutes to record a single 2D fluorescence spectrum in an excitation light wavelength range of 250-730 nm with an excitation step size of 10 nm.

For a microtiter plate comprising 48 microreactors (wells), with each microreactor, it would only be possible to conduct one measurement, i.e. measure one 2D fluorescence spectrum, every 20.2 h. This time interval is clearly too long to allow monitoring of parallel cultivations in microtiter plates online.

By means of the method according to the invention and a device for carrying out the method, the time required to record a complete 2D fluorescence spectrum in the excitation range of 250-730 nm with an excitation step size of 10 nm can be reduced to 24 sec per microreactor. Using the present invention, it is therefore possible to measure a complete microtiter plate comprising 48 microreactors in 30 min.

In the following table, the times required to record 2D fluorescence spectra for a 48-well microtiter plate and a 96-well microtiter plate are shown in a comparison of the prior art and the present invention:

|  | Prior art | Present invention |
| --- | --- | --- |
| Spectral recording/well | 25 min | 0.4 min |
| Spectral recording/48-well MTP including positioning time | 1210 min (20.2 h) | 30 min (0.5 h) |
| Spectral recording/96-well MTP including positioning time | 2420 min (40.3 h) | 60 min (1.0 h) |

In an advantageous embodiment of the invention, the monochromatic excitation light, the excitation wavelength of which is modified step by step, is generated by means of an automatically tunable monochromator for spectral isolation of different wavelengths from the incident light of a light source. The transfer and introduction of the excitation light into the individual microreactors and the transfer of the emission spectrum from the microreactor to the optical element are carried out using a beam guidance system. The beam guidance system comprises an optical coupler, at least one optical waveguide and optionally further optical elements, such as e.g. semitransparent mirrors. The optical coupler, configured to introduce the excitation light into the liquid culture of a microreactor and to couple the emission spectrum of the liquid culture into the beam guidance system, can for example be composed of an end of one or a plurality of optical waveguides oriented with respect to the microreactor. Alternatively, lenses or lens arrangements can form the optical coupler. As the coupler is not moved during recording of the 2D fluorescence spectrum, the microreactor moves relative to the optical coupler. After measurement of the 2D fluorescence spectrum, the optical coupler is moved to another microreactor. In order to ensure regular fluid circulation during agitation, the microreactors preferably do not show strong current disturbances or have a round cross-section.

In order to increase the number of parallel cultivations, a plurality of microtiter plates can be attached to one microreactor platform, wherein the microreactors of all of the microtiter plates are sequentially measured by means of a measuring device. By means of the x-y positioning unit, the coupler of the measuring device is moved from microreactor to microreactor not only beneath a single microtiter plate, but beneath a plurality of microtiter plates. For example, if four microtiter plates with 48 microreactors are attached to one microreactor platform, a total of 192 parallel cultivations can be carried out.

However, the time interval between two measurements of the same microreactor increases with the number of parallel cultivations. In an embodiment of the invention, in order to increase the measurement frequency, a plurality of measuring devices is therefore provided, allowing the simultaneous recording of 2D fluorescence spectra in different microreactors. If the optical couplers of the plurality of measuring devices are moved by means of a positioning unit between the microreactors of one or a plurality of microtiter plates, the different microreactors can be synchronously started up, and orientation of each coupler beneath the microtiter plate can be carried out in the same manner. In this embodiment of the invention, 2D fluorescence spectra can be simultaneously recorded in a plurality of microreactors of one or a plurality of microtiter plates.

A further possibility for reducing the time required for measuring the liquid cultures of an entire microtiter plate is that of measuring a plurality of microreactors without repositioning the coupler. For this purpose, the agitation diameter of the orbital shaker is adjusted such that a plurality of microreactors, during one rotation of the orbital, shaker, successively circle above the optical coupler, wherein the recorded fluorescence spectra are assigned to the microreactors circling above the optical coupler.

In order to improve the measurement results, in an advantageous embodiment of the invention, the time of measurement and the agitator position are synchronized. The position of the liquid culture in the microreactor depends on the agitator position. In order to carry out this synchronization, introduction of the excitation light is interrupted depending on the position of the orbital shaker. The interruption is carried out in particular by means of a shutter. The shutter is a light-impermeable, mechanically moveable element for interrupting the optical path of the excitation light. Alternatively, however, the light source for producing the excitation light can be clocked depending on the agitator position. The position of the orbital shaker is determined by means of a position sensor. Suitable means for determining the position include a Hall effect sensor and a magnet attached to the shaft of the orbital shaker. Alternatively, a light barrier can be used. A substantial advantage of synchronizing the introduction of the excitation light with the position of the orbital shaker is that clearly defined areas of the microreactor can be measured, for example the liquid sickle of the liquid culture that forms during the agitating motion.

In measuring the 2D fluorescence spectra with a measuring device according to the invention, it is inevitable that in each measurement, reflected excitation light is absorbed by the sensor matrix. In particular, in the case of high cell densities in a liquid culture, strong backscattering of the introduced excitation light may occur, which may cause individual sensors of the sensor matrix to be overloaded. This overloading can result in measurement errors in adjacent sensors of the matrix. In an advantageous embodiment of the invention, the excitation wavelength in the emission spectrum is therefore masked. With respect to the continuously changing excitation wavelength, by selectively modifying the position of the optical element, the region of the emission spectrum having a wavelength less than or equal to the excitation wavelength can preferably be guided past the sensor matrix. Alternatively, the excitation wavelength can be masked by means of a moveable screen between the optical element and the sensor matrix. The masking of the excitation wavelength provided according to the invention allows higher intensities of the excitation light. The greater excitation intensity results in emission spectra with stronger fluorescence signals and ultimately improved measurement values (2D fluorescence spectra).

In order to increase the energy density of the excitation light, it is provided in an advantageous embodiment that the excitation light is collimated or focused prior to introduction into the liquid culture. A collimator is particularly suitable as a lens for collimating the excitation light. The higher energy level of the excitation light is particularly advantageous in cases where, during one rotation of the orbital shaker, a 2D fluorescence spectrum is to be recorded by means of a measuring device in a plurality of microreactors circling above the coupler. In addition, the emission spectrum to be coupled into the beam guidance system, in particular the optical waveguide, can be concentrated.

In an advantageous embodiment of the invention, the backscattering of the excitation light irradiated into the liquid cultures is measured by means of a separate photosensitive sensor of the measuring device. Data on the growth behavior or morphology of microorganisms during the reaction in the culture medium of the liquid culture can be obtained from this backscattering. The light scattering is preferably transferred via a further optical waveguide to the photosensitive sensor.

The optical waveguide for introducing the excitation light and the further optical waveguide for transferring the backscattering are preferably arranged with respect to each other in the coupler of the beam guidance system such that the two optical waveguides focus on one point. This arrangement is advantageous in that no reorientation of the coupler is required for measurement of the backscattering, thus allowing the two measurements to be carried out at shorter intervals. Alternatively, the optical waveguide can be arranged such that by means of the movable optical elements, scattered light guided past the sensor matrix or scattered light reflected by the screen is coupled into one end of the optical waveguide.

The beam guidance system can be configured to have two separate optical waveguides, one for the excitation light and one for the emission spectrum, or one y-shaped optical waveguide with separate fibers for the excitation light and the emission spectrum. In an alternative embodiment of the beam guidance system, the excitation light is deflected by a semitransparent mirror and introduced into the liquid culture via an optical waveguide with only one fiber. In the beam guidance system, the emission spectrum is transferred through the one optical waveguide and the semitransparent mirror to the optical element that fans the emission spectrum out on the sensor matrix. Compared to a beam system with a y-shaped optical waveguide, as the excitation light and the emission spectrum are transferred via only one fiber, the total radius of the one optical waveguide can be reduced compared to the two-fiber y-shaped optical waveguide, thus allowing the excitation radiation to be better focused. Crosstalk with adjacent microreactors can be prevented.

By integrating a pipetting robot into the device, it becomes possible during the reaction to automatically take samples of the liquid culture from the individual microreactors at different times using the pipetting robot that are analyzed off line with respect to specified process parameters. Moreover, addition of material is also possible.

For calibration of the method, chemometric models can be prepared in a minimal period of time from the 2D fluorescence spectra recorded at the different sampling times.

In chemometric modelling, mathematical and/or statistical relationships between the process parameters analyzed offline and the 2D fluorescence spectra of the liquid cultures in the individual microreactors recorded at the different sampling times are determined. The chemometric model then makes it possible to determine process parameters of the liquid culture from a 2D fluorescence spectrum.

When reactions of liquid cultures are carried out in parallel under the same conditions in a plurality of microreactors, the data density can be increased by measuring the 2D fluorescence spectra of the liquid cultures recorded offset in time in these microreactors over a time vector and evaluating them.

In order to allow offline analyses of individual samples to be completely dispensed with for calibration of the method, it is proposed in an embodiment of the invention to carry out reactions in the liquid cultures in a plurality of microreactors under the same conditions, wherein the initial values of the process parameters to be measured, for example the concentrations of nutrients or (by)products, are different in the plurality of microreactors. The effect of the different initial values on the recorded 2D fluorescence spectra is used for developing the chemometric model.

A further possibility for preparing a chemometric model without offline analyses of samples of the liquid cultures is to carry out reactions in the cultures in a plurality of microreactors under the same conditions, wherein an analyte is added at different times to individual microreactors among the above-mentioned microreactors that modifies the process parameter to be measured in the culture in a defined way, so that for example known jumps in concentration occur. The result is that the reactions in the different microreactors no longer occur under the same conditions. The effect of the defined modification of the process parameter on the recorded 2D fluorescence spectrum of the respective liquid culture is then used for preparing the chemometric model.

A further possibility for calibration without offline analysis of process parameters is that of using a mechanistic/mathematical model to describe the functional context underlying the modification of a process parameter in one of the liquid cultures. At the beginning of the reaction, model parameters are assumed for the mechanistic/mathematical model that may be false. The process parameters determined based on the mathematical model are compared with the 2D fluorescence spectra recorded at different times during the reaction, and the model parameters are continuously corrected depending on this comparison. The result is that the process can be better depicted with each measured 2D fluorescence spectrum. On completion of calibration, a mechanistic/mathematical model that describes the process well is also provided in addition to a chemometric model.

By means of the method according to the invention, it is possible to use a chemometric model for determining not only the concentration of individual substances, but also respiratory activity, for example the oxygen transfer rate (OTR), based on the on the recorded 2D fluorescence spectra. The complex equipment ordinarily needed to determine respiratory activity is not required, and the respiratory activity can be directly determined from the recorded 2D fluorescence spectra in the respective culture based on a chemometric model previously determined by means of calibration.

BRIEF DESCRIPTION OF THE DRAWINGS

In the following, the method according to the invention and a device for carrying out the method are explained in greater detail with reference to the figures. In the drawings:

FIGS. 4A, 4B and 4C are schematic diagrams showing a measurement in a plurality of microreactors without repositioning a coupler of a beam guidance system of the device according to FIG. 1, FIGS. 5A and 5B are schematic diagrams of two embodiments of an optical unit according to FIG. 2 that are configured for masking backscattering.

DETAILED DESCRIPTION OF THE PREFERRED EMBODIMENTS

Figure 1:
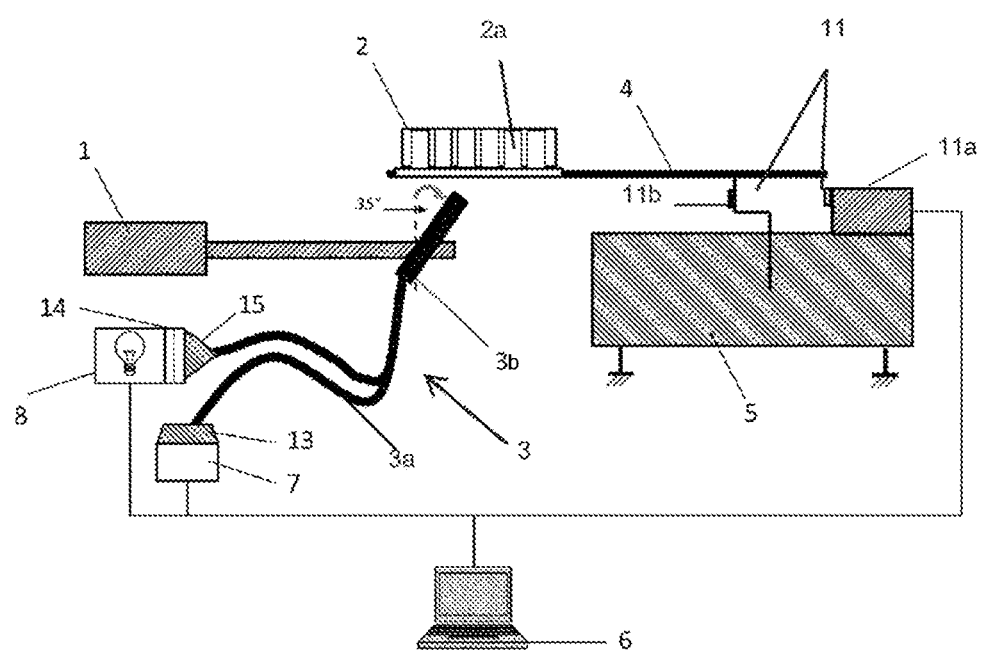
FIG. 1 is a schematic diagram of a device according to the invention for determining process parameters by means of 2D fluorescence spectroscopy (measurement) in liquid cultures in a plurality of microreactors of an agitated microtiter plate.

FIG. 1 shows a schematic structure of a device according to the invention for determining process parameters, such as e.g. substrate, protein and biomass concentration and substance transfer rates, by means of 2D fluorescence spectroscopy in a plurality of different liquid cultures in microreactors of an agitated microtiter plate.

The device comprises a microreactor platform (4) connected to an orbital shaker (5) on which at least one microtiter plate (2) with a plurality of microreactors (2*a*) is arranged. At least the bottom surfaces of the microreactors (2*a*) of the microtiter plate are transparent to electromagnetic radiation that is emitted and received by a measuring device. The measuring device comprises a light source (8) and an automatically tunable monochromator (15). The monochromator (15) is designed for spectral isolation of different wavelengths from the incident light of the light source (8) in order to produce monochromatic excitation light, the excitation wavelength of which is automatically modified step by step. The measuring device further comprises a beam guidance system (3), which is composed in the example shown of a y-shaped optical waveguide (3*a*) and a coupler (3*b*). The optical fibers of the two strands of the y-shaped optical waveguide (3*a*) run together in the area of the coupler (3*b*).

The beam guidance system (3) respectively transfers the excitation light from the monochromator (15) to the liquid culture in one of the microreactors (2*a*) of the microtiter plate (2) and transfers the emission spectrum from the liquid culture in the respective microreactor (2*a*) to an optical element (13), for example a prism or a lattice. The optical element (13) decomposes the emission spectrum (16) for each excitation wavelength into the different wavelengths and depicts the fanned (spread) out emission spectrum on a sensor matrix (7) that in particular is configured as a CCD sensor. Evaluation of the recorded signals of the sensor matrix is carried out by means of a computer (6).

The coupler (3*b*) of the beam guidance system (3) is arranged on an x-y positioning unit (1) at an acute angle of e.g. 35 degrees from the vertical and is selectively oriented with respect to the transparent bottom surfaces of the individual microreactors (2*a*).

Furthermore, between the light source (8) and the tunable monochromator (15) is a shutter (14), which is configured to carry out interruption of the excitation light that is controlled by the computer (6) or the CCD camera comprising the sensor matrix (7) depending on the position of the microreactor platform (4). The position of the microreactor platform (4) is measured using a position sensor (11), which in the example shown is composed of a magnet (11*b*) and a Hall effect sensor (11*a*) arranged on the shaft of the orbital shaker.

Of course, other techniques are also suitable for positional monitoring of the shaker, in particular optical or inductive positional measurements.

Figure 2:
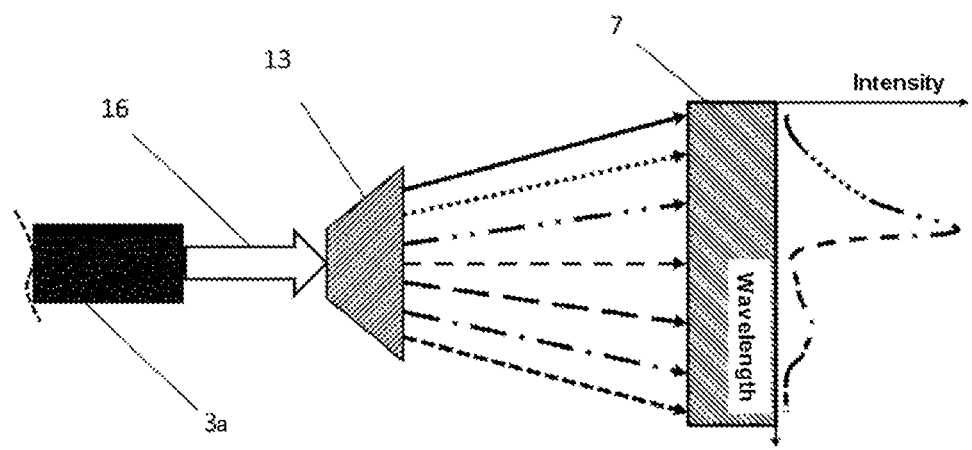
FIG. 2 is a schematic diagram of an optical unit for recording a 2D fluorescence spectrum in a device according to FIG. 1, FIGS. 3A and 3B are two respective views of a measurement segment within a microreactor.

FIG. 2 shows how the emission spectrum (16) is coupled from the optical waveguide (3*a*) into the optical element (13). The optical element (13) separates the emission spectrum (16) into its individual wavelengths and fans it out over the sensor matrix (7). This optical arrangement gives rise to bands for the individual wavelengths on the sensor matrix (7), and the intensity of the emission spectrum at the different wavelengths can be determined by means of the sensor matrix (7). The structure composed of an optical element (13) and the sensor matrix (7) shown in FIG. 2 allows simultaneous recording of a complete emission spectrum after excitation of the liquid culture by an excitation radiation having an excitation wavelength. Measurement can be conducted in a significantly shorter period of time due to the simultaneous measurement of the intensities of the different wavelengths of each emission spectrum.

By means of a shutter (14), the recorded 2D fluorescence spectra are synchronized in a computer-supported manner with the position of the microreactor platform (4) and thus of the liquid culture in the respective microreactor (2a). Depending on the shaker/liquid position relative to the position of the optical coupler (3a), the optical path of the excitation light is opened for a specified period of time using the mechanical shutter (14). This synchronization ensures that during measurement, the excitation light will strike the microreactor (2a), which rotates above the stationary coupler (3b), at a specified time and in a specified position. After measurement of the emission spectrum (16), i.e. after completion of the measurement, the optical path of the excitation light is again closed by the mechanical shutter (14), so that excitation radiation can no longer reach the microreactor (2a). A substantial advantage of synchronization is that a defined measurement segment (18) of the microreactor (2a), as shown schematically in FIGS. 3A and 3B, can be investigated, thus for example making it possible to selectively take into account the liquid sickle (17) of the liquid culture rotating in the microreactor (2a). The measurement segment (18) is the area in which, during measurement of an emission spectrum, the excitation light is coupled in a position-controlled manner into one of the microreactors (2a) of an agitated microtiter plate (2).

Figure 3A:
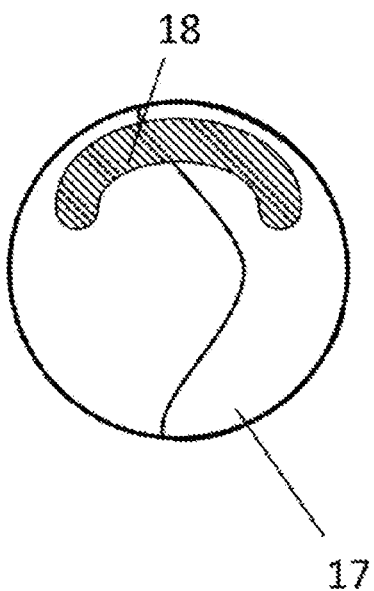
Figure 3B:
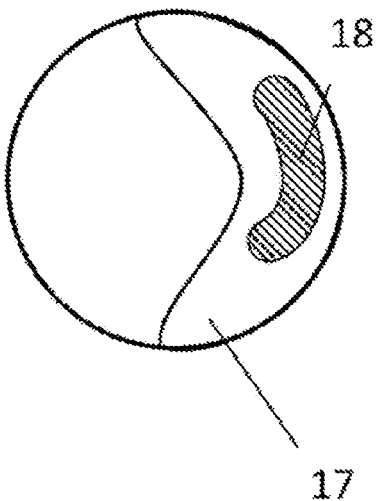

FIGS. 3A and 3B shows two measurement segments (18). By means of an adjustable delay in the start of measurement, using the information from the position sensor, the measurement can be selectively initiated at each position during rotation of the microreactor (2a) above the coupler (3b). By varying the integration time of the measurement signals of the sensor matrix (7), measurement signals of different lengths can be investigated within each microreactor (2a). In FIG. 3A, as the measurement segment (18) extends from the empty microreactor (2a) into the liquid sickle (17), the emission spectrum can be distorted. According to FIG. 3B, the measurement segment (18) lies exclusively within the liquid sickle (17), so that only the emission spectrum of the liquid culture is recorded during measurement, which is desirable.

In an embodiment of the invention, in order to reduce the time required for recording the emission spectra (16) of the liquid cultures in all of the microreactors (2a) of a microtiter plate (2), a plurality of microreactors (2a) can be investigated without repositioning the coupler (3b). Time is advantageously saved because less time is required for repositioning the coupler (3b) beneath the microreactors (2a). According to this measurement principle, it is advantageous to position the coupler (3b) beneath the microtiter plate (2) in such a way that the excitation light is vertically incident on each microreactor (2a). This structure is schematically shown in FIG. 4A. Moreover, the position of the coupler (3b) relative to the agitated microtiter plate (2) is selected such that the center of the rotational movement of the microtiter plate (2) lies exactly between a plurality of microreactors (2a), as shown in FIG. 4B for two microreactors and in FIG. 4C for four microreactors. In a device configured as shown in FIGS. 4A, 4B and 4C as the electromagnetic radiation (19) of the excitation light is successively introduced into a plurality of microreactors (2a) for each rotation of the orbital shaker (5), a plurality of microreactors (2a) can be measured without repositioning the coupler (3b). Fewer movements of the coupler (3b) by the x-y positioning unit (1) are therefore required to measure all of the microreactors (2a) of a microtiter plate (2), allowing the measurement to be substantially accelerated. As shown in FIG. 4C, for example, if the coupler (3b) is positioned in the center of four adjacent microreactors (2a), it is then necessary for the x-y positioning unit (1) to move to only 24 instead of 96 positions in order to measure all of the microreactors of a 96-well microtiter plate. This results in considerable savings of time in measuring all of the microreactors (2a) of the microtiter plate (2). Assignment of the emission spectra from the respective microreactors (2a) during a rotation of the microreactor platform (4) can be carried out using the position sensor (11). The position sensor (11) measures which microreactor (2a) is in the focus of the coupler (3b) at which point in time. A further advantage of having a plurality of microreactors (2a) circling above an optical coupler (3b) is that larger agitation diameters (preferably 6 mm, 9 mm, 12.5 mm or larger) can be used. Larger agitation diameters mean that lower rotational speeds of the orbital shaker (5) are required in order to produce a rotating liquid sickle (17) in the microreactors (2a). Moreover, larger agitation diameters are particularly suitable for investigating liquid cultures of high viscosity, such as those that can occur for example in cultivation of biopolymers or filamentous organisms.

In the structure shown in FIG. 1, reflected excitation light (scattered light) is inevitably recorded in each measurement. In particular, high cell densities of the liquid culture lead to strong backscattering that can lead to measurement errors in recording of the emission spectrum by means of the sensor matrix (7). In order to avoid such measurement errors, as shown in FIG. 5A, one can work with a moveable optical element (13). The moveable optical element (13) makes it possible to exclude from measurement of the emission spectrum the region of electromagnetic radiation of the emission spectrum having a wavelength less than or equal to the excitation wavelength. The modifiable position of the optical element (13) makes it possible to selectively guide the radiation having a wavelength less than or equal to the excitation wavelength past the sensor matrix (7). In this way, the intensity of the excitation light and thus the intensity of the emission spectrum can be increased, and ultimately, the sensitivity of the measuring device can be improved. Movement of the optical element (13) is carried out depending on the excitation wavelength of the introduced excitation light. In this method, the assignment of the wavelength to a position (pixel) on the sensor matrix (7) must be recalculated with respect to the wavelength of the excitation light.

Figure 5B:
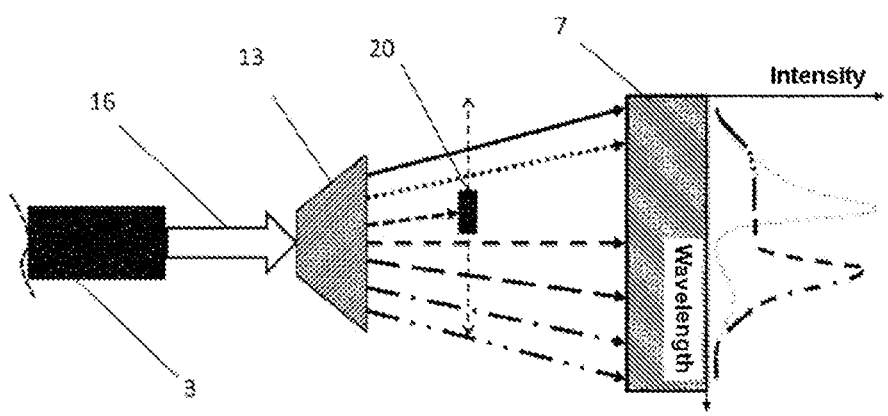
Figure 5A:
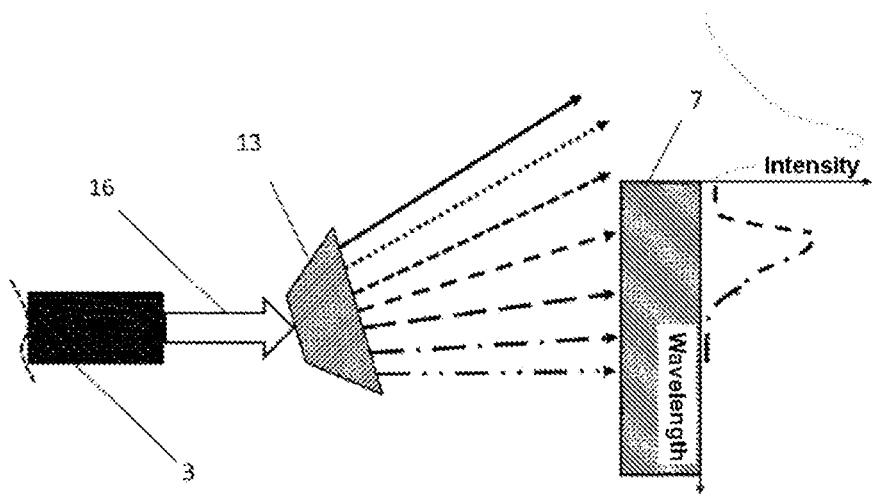

FIG. 5B shows an alternative embodiment for reducing backscattering. In this case, a screen (20) is arranged between the optical element (13) and the sensor matrix (7) that masks light of the respective excitation wavelength so that this light does not reach the sensor matrix (7). By means of a stepping motor, the screen (20) is preferably moved during introduction of each excitation wavelength in such a way that the optical path of the exciting wavelength between the optical element (13) and the sensor matrix (7) is blocked. This structure allows a higher intensity of the excitation light and thus a higher intensity of the emission spectrum, which leads to stronger fluorescence signals and ultimately to improved measurement values.

Figure 6A:
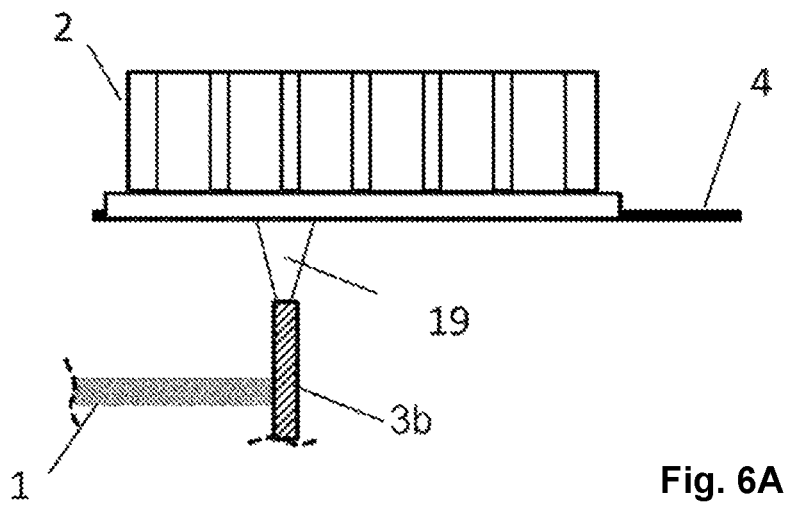
FIGS. 6A and 6B are schematic diagrams showing two embodiments of a use of optically active components for improving measurement sensitivity.
Figure 6B:
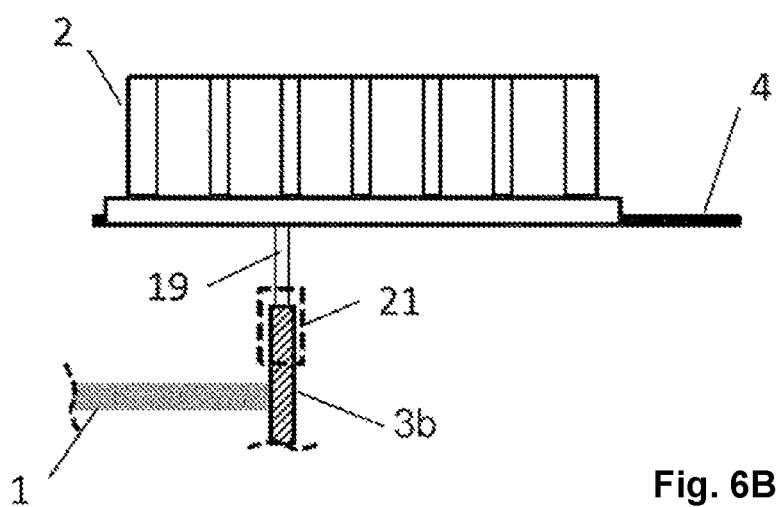

FIG. 6B shows the use of additional optically active components, such as e.g. a collimator (21), which collimates the electromagnetic radiation (19) of the excitation light. The collimator (21) is attached to the end of the optical waveguide (3a) in the area of the coupler (3b). The collimation makes it possible to introduce the excitation light into the liquid cultures with a high energy intensity. In addition, the collimator (21) can focus the coupled-in emission spectrum (16) so as to capture larger portions of the emission spectrum. The reduction in size of the measurement segment by the collimator (21) with simultaneously increased intensity of the excitation light can be particularly advantageous in cases where the coupler (3b) according to FIGS. 4A, 4B and 4C is positioned such that, during one rotation of the orbital shaker, (5) the fluorescence spectra of the liquid cultures in a plurality of microreactors (2a) are recorded. The smaller and more sharply delimited measurement segment (18) allows a wider selection of different agitation diameters and longer measurement segments in the circumferential direction.

Figure 7:
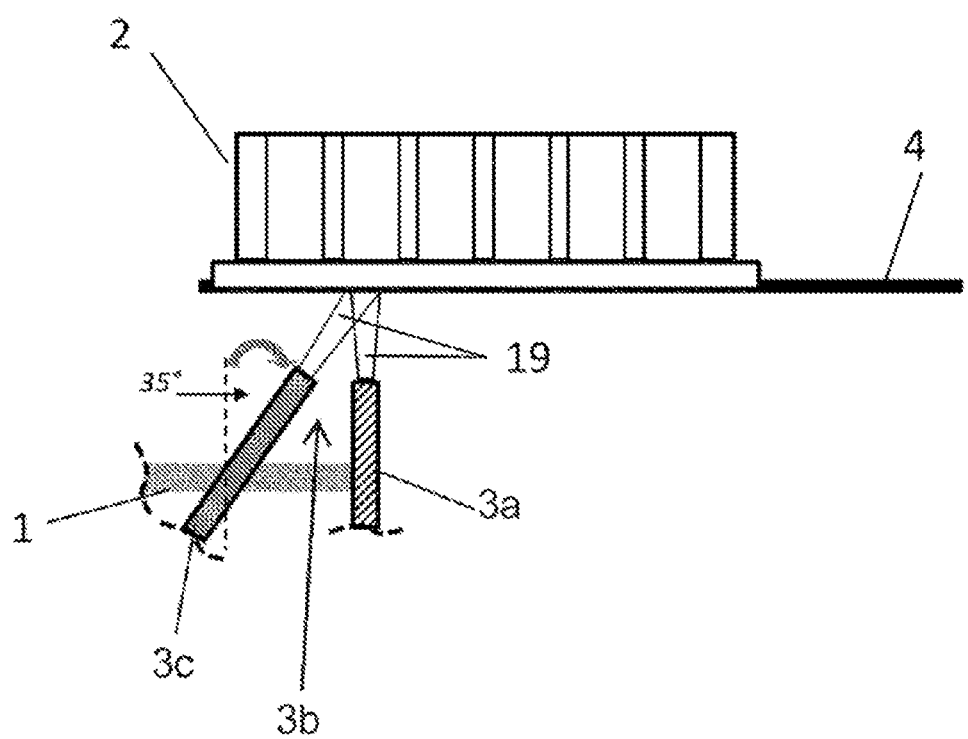
FIG. 7 is a schematic diagram of an arrangement of optical waveguides for simultaneous measurement of an emission spectrum and the backscattering beneath the microtiter plate.

By means of the measures shown in FIGS. 5A and 5B backscattering of the excitation light onto the sensor matrix (7) is almost completely eliminated. However, useful information, such as information on the growth behavior or morphology of microorganisms during cultivation, can be obtained from the backscattering. FIG. 7 shows a device in which the backscattering of the electromagnetic radiation (19) irradiated into the liquid culture of a microreactor (2a) is measured using a separate photosensitive sensor not shown in FIG. 7. The backscattered excitation light is supplied to the photosensitive sensor by means of a further optical waveguide (3c). For recording the backscattering, the additional optical waveguide (3c) is oriented in the coupler (3b) with a setting angle of e.g. 35 degrees from the vertical. In this case, the setting angle of the optical waveguide (3a) for fluorescence measurement is 0 degrees from the vertical. This orientation of the optical waveguide (3a) in the coupler (3b) improves the focusing and recording of the emission spectrum. It can further be seen from FIG. 7 that the optical waveguides (3a, 3c) are oriented in the coupler (3b) in such a way that the focus of the two waveguides is on one point. Accordingly, the focus can be oriented to exactly the same position within the microreactor (2a). This is advantageous in that for measurement of the backscattering, it is not necessary to reposition the coupler (3b) beneath the microtiter plate, with the result that measurement of the backscattering is not accompanied by an increase in the measuring time.

Using the structure shown in FIG. 7, fluorescence spectra can be recorded with a high intensity of the excitation light, and the backscattering can be determined in an optimal manner.

Figure 8:
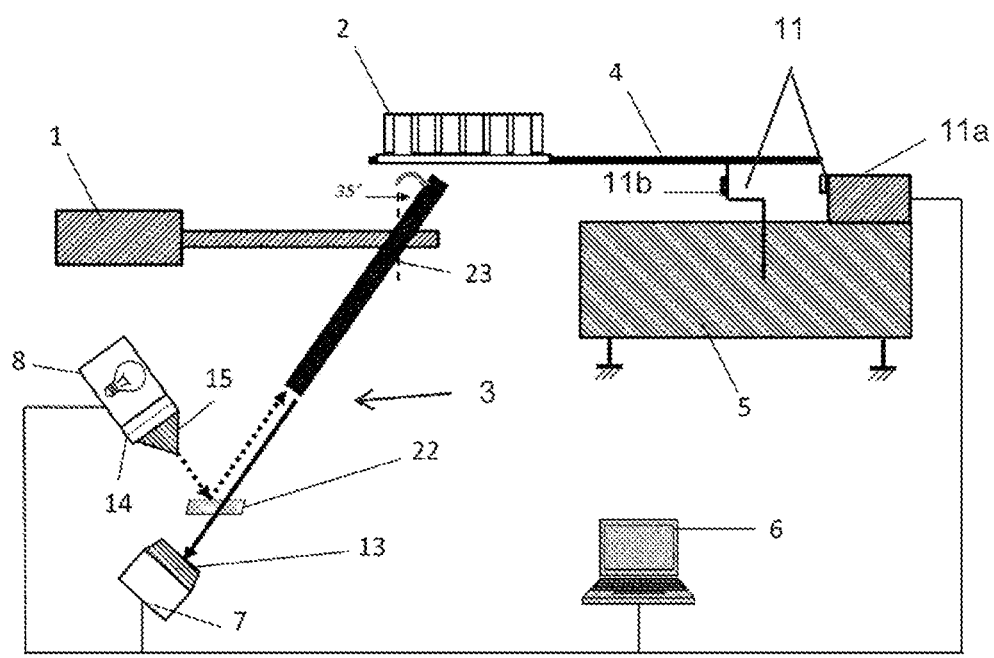
FIG. 8 is a schematic diagram of the device according to FIG. 1 with a different beam guidance system.

FIG. 8 shows a device for carrying out the method according to FIG. 1, but with a beam guidance system (3) having a different structure. The excitation light from the light source (8) is deflected by a semitransparent mirror (22) and introduced via an optical waveguide (23) with only one fiber into the liquid culture in one of the microreactors (2a). The emission spectrum (16) of the liquid culture is transferred through the optical waveguide (23) and the semitransparent mirror (22) to the optical element (13), and finally to the sensor matrix (7). The single fiber of the optical waveguide (23) is thicker than the fibers of the fiber bundle of the optical waveguide (3a) according to FIG. 1. This allows the radius of the optical waveguide (23) as a whole (and thus the radius of the electromagnetic beam) to be reduced and thus allows the radiation to be better focused. This improved focusing prevents crosstalk with adjacent microreactors.

In order to further increase the number of parallel cultivations, a plurality of microtiter plates (2) can be arranged together on a microreactor platform (4), wherein the microreactors (2a) of all of the microtiter plates (2) are sequentially measured. The coupler (3b) is no longer moved only beneath one microtiter plate (2) from microreactor (2a) to microreactor (2a), but beneath a plurality of microtiter plates (2). For example, if four 48-well microtiter plates are arranged on the microreactor platform (4), a total of 192 parallel cultivations can be carried out and measured.

Figure 9:
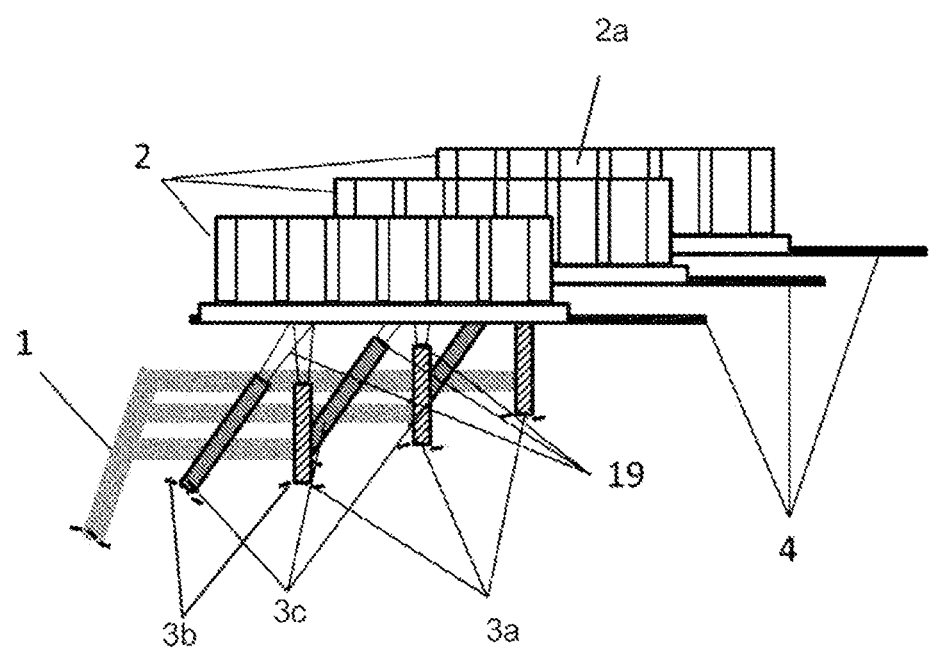
FIG. 9 is a schematic diagram of a device according to the invention for simultaneously determining process parameters by means of 2D fluorescence spectroscopy in liquid cultures in a plurality of microreactors, wherein the microreactors are arranged on different microtiter plates.

As the number of cultivations carried out in parallel increases, however, the time between two measurements in the same microreactor also increases. In order to increase the measurement frequency, FIG. 9 shows a device with which 2D fluorescence spectra of the liquid cultures can be simultaneously recorded in different microreactors (2a) of a plurality of microtiter plates (2) by means of a plurality of measuring devices. The optical waveguide (3a) for fluorescence measurement and the optical waveguide (3c) for measurement of backscattering are arranged on moveable arms of an x-y positioning unit (1) in such a way that microreactors (2a) can be simultaneously measured on different microtiter plates (2). As the optical waveguides (3a, 3c) are fastened to an x-y positioning unit (1), the microreactors (2a) of different microtiter plates (2) are approached synchronously and simultaneously. This means that in the example shown, three microreactors (2a) are simultaneously measured after each positioning, wherein the microreactors are located at the same positions in the different microtiter plates (2). As all of the microtiter plates (2) are located on the microreactor platform (4) of an orbital shaker (5), the measurements can be initiated at the same type and synchronized by means of a single position sensor (11).

Figure 10A:
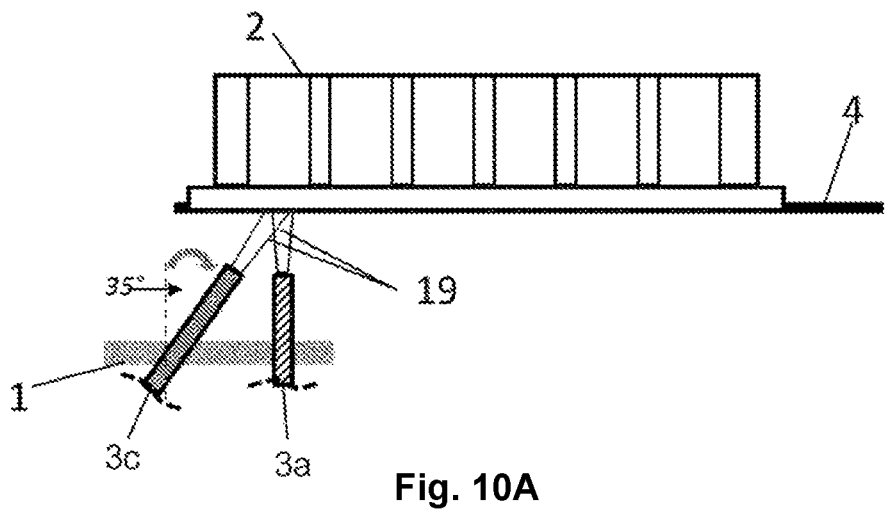
FIGS. 10A and 10B are schematic diagrams illustrating a measurement of only one liquid culture on a microtiter plate and simultaneous measurement of a plurality of liquid cultures in different microreactors on a microtiter plate respectively.
Figure 10B:
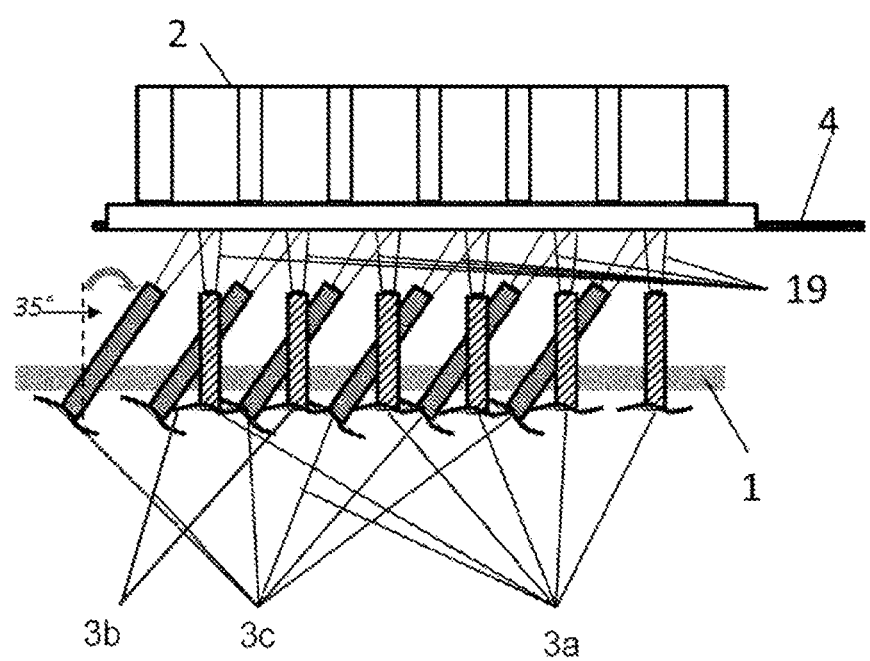

FIG. 10B shows a further possibility for increasing the recording rate of the fluorescence spectra in a microtiter plate (2a). Instead of only one measuring device as shown in FIGS. 10A, in embodiment of FIG. 10B the optical couplers (3b) of a plurality of measuring devices are attached to the arm of a positioning unit (1) at an identical distance from the centers of the microreactors (2a) and are moveable between the microreactors (2a) of a single microtiter plate (2). Using the structure shown in FIG. 10B, provided that a corresponding number of couplers (3b) and measuring devices are present, entire rows or columns of the microreactors (2a) of a microtiter plate (2) can simultaneously be measured. In this case, moreover, the positioning unit need only move the couplers (3b) in one direction in order to completely measure a microtiter plate.

Using the six optical waveguides for the measurement of backscattering (3c) and the six optical waveguides for fluorescence measurement (3a) shown in FIG. 10B, the fluorescence and/or backscattering can be measured simultaneously in a complete row of the microtiter plate (2). In the case of a 48-well microtiter plate (2), the optical waveguides (3a, 3c) must therefore only be moved in one dimension by means of the positioning unit (1). The time saved in this manner results in increased measurement frequency and data density.

In an advantageous embodiment of the invention, the device comprises a pipetting robot in order to automatically take samples of the liquid cultures from the microreactors (2a) at different times during cultivation or add water or solutions containing e.g. nutrients or (by)products. The combination of the method according to the invention with the automatic sampling allows accelerated preparation of chemometric models. From the ongoing cultivation, samples can automatically be taken from the liquid culture at different times for an offline analysis. Chemometric models can be prepared from the process parameters of the samples analyzed offline and the 2D fluorescence spectra recorded at the various sampling or addition times.

Figure 11:
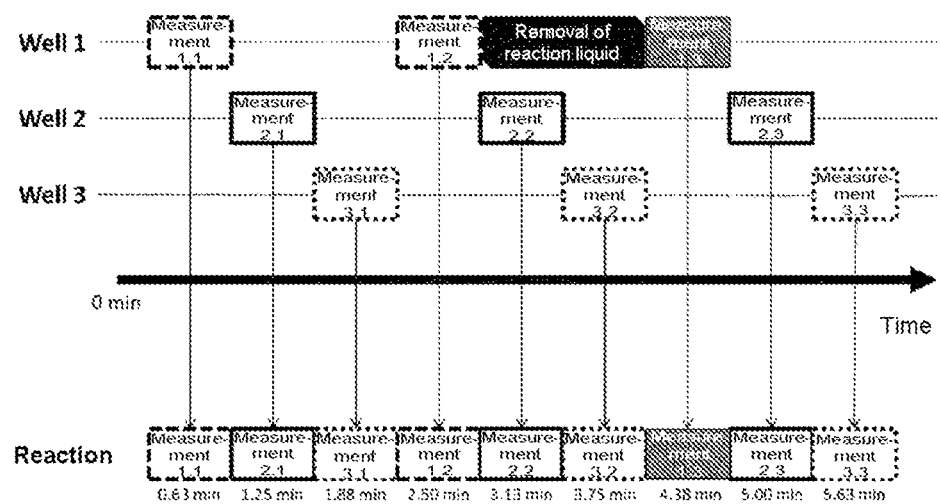
FIG. 11 is a schematic diagram illustrating the increase in the data density of measurements of the same reactions in different microreactors.

In order to obtain a higher temporal data density in observation of the same reactions in liquid cultures, FIG. 11 schematically shows a method in which cultivations of liquid cultures are carried out in a plurality of microreactors (well 1 to well 3) under the same conditions. From each of the above-mentioned liquid cultures in wells 1-3, 2D fluorescence spectra (measurement) are recorded offset in time: for example, measurements 1.1 to 1.3 for the microreactor (well 1), measurements 2.1 to 2.3 for the microreactor (well 2), and measurements 3.1 to 3.3 for the microreactor (well 3). The 2D fluorescence spectra 1.1 to 1.3 recorded in wells 1 to 3 offset in time are combined in such a way that the 2D fluorescence spectra from the different wells 1 to 3 are measured using a common time vector. In this way, although the well-related resolution of the measurements is lost, the intervals between two measurements can be significantly reduced.

The method shown in FIG. 11 is particularly advantageous for preparing chemometric models. For each well 1 to 3, three measurements are shown, i.e. the recording of three 2D fluorescence spectra. The entire liquid culture is removed from well 1 after the second measuring cycle, i.e. after 3.13 min, in order for example to conduct offline analyses of this sample. The total of nine individual measurements, three measurements per microreactor respectively (wells 1 to 3), are combined into one reaction course on the time axis. In order to develop the chemometric model, one can make use of a total of eight measurements during reaction. Measurement 1.3 is not taken into account in preparing the model, because at the time of this measurement, there was no longer any reaction liquid present in the microreactor (well 1) and it was therefore impossible to determine any useable measurement values.

Figure 12:
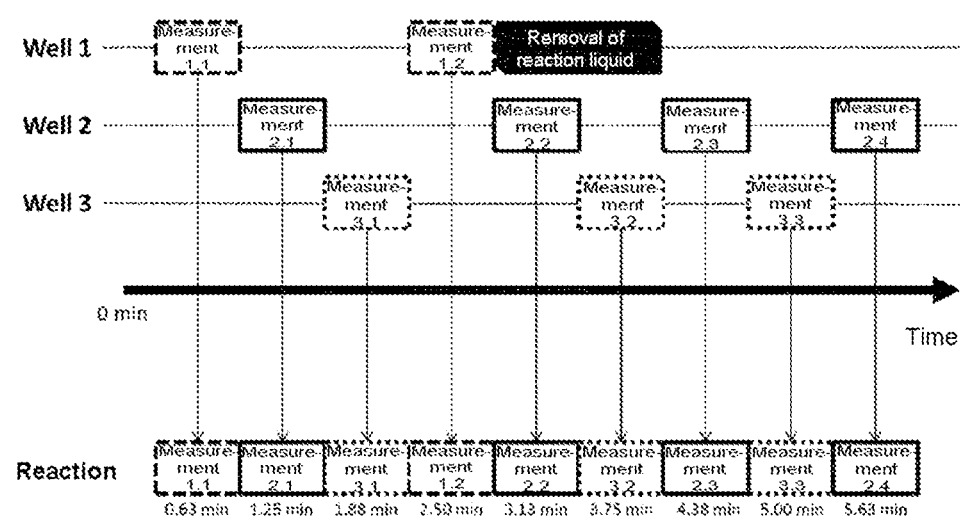
FIG. 12 is a further schematic diagram illustrating the increase in the data density of measurements of the same reactions in different microreactors omitting measurements in empty microreactors.

FIG. 12 shows a method according to FIG. 11 in which a increase in data density can be achieved by no longer measuring the microreactor (here: well 1) after the reaction liquid is removed. In this method, instead of carrying out a superfluous measurement in the microreactor (well 1) after removal of the reaction liquid, a measurement is carried out directly in the microreactor (well 2). In this manner, a further measurement (measurement 2.4) can be carried out in well 2 within 5.63 min. Accordingly, nine usable measurements are available for preparing the chemometric model.

Figure 13A:
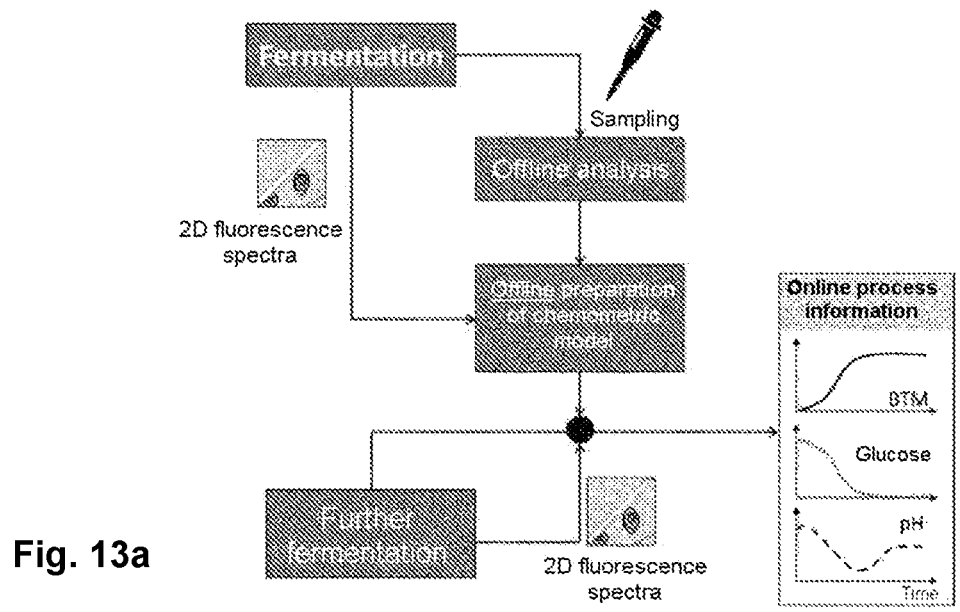
FIGS. 13A and 13B are schematic diagrams illustrating a conventional approach for preparing a chemometric model based on 2D fluorescence spectra in individual stirred vessel fermenters and the approach for preparing a chemometric model according to an embodiment of the present invention respectively.
Figure 13B:
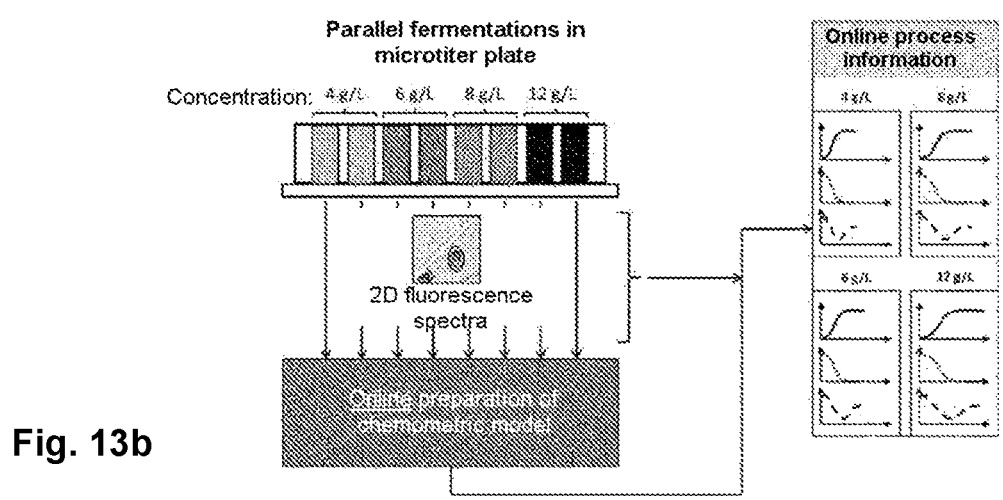

In contrast to the conventional approach for preparing chemometric models based on 2D fluorescence spectra in individual stirred vessel fermenters (FIG. 13A), FIG. 13B shows a method in which cultivations in the liquid cultures in a plurality of microreactors (2a) of a microtiter plate (2) are carried out under the same conditions, wherein the initial values of the process parameters to be measured (e.g. concentration of C source, products or byproducts) in the liquid cultures of the individual microreactors are different. In use of 2D fluorescence spectroscopy with conventional individual fermenters, this method involves unacceptable complexity with respect to experimentation and time required. However, the parallel cultivation in the microreactors of the microtiter plate according to the present invention makes this type of approach possible without problems. The effects of the concentration differences in the analytes of interest on the 2D fluorescence spectra are used online for developing chemometric models that are developed during the experiment. In this method variant, calibration is carried out during determination of the process parameters by means of 2D fluorescence spectroscopy.

Figure 14:
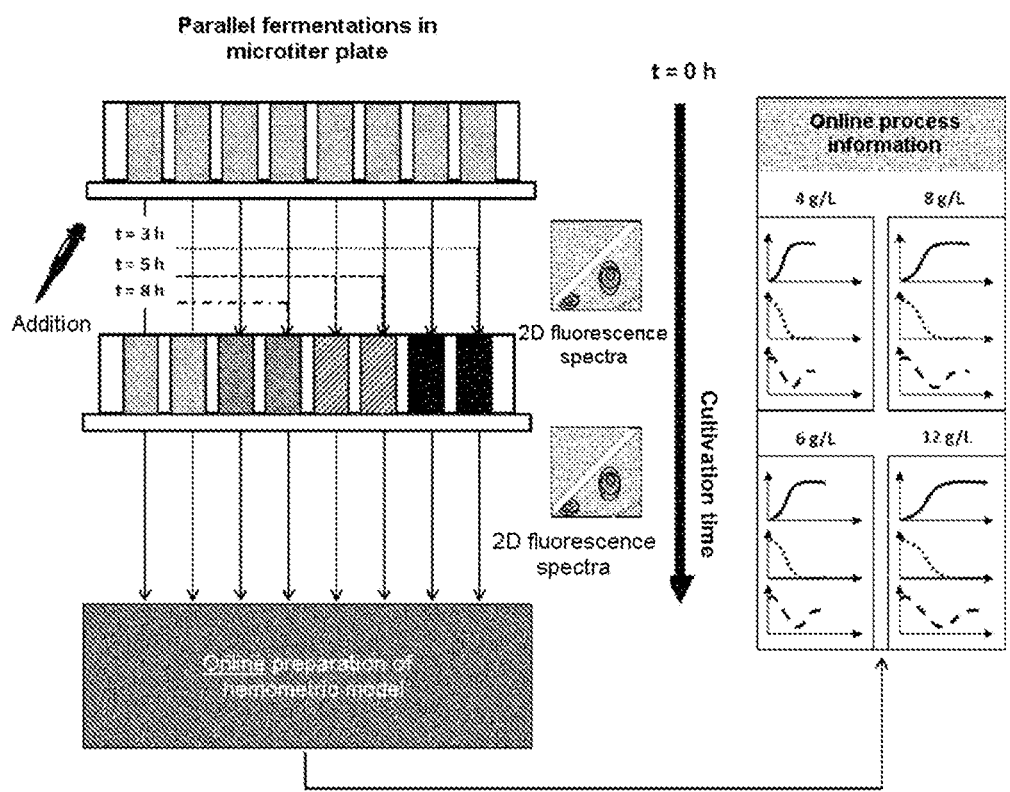
FIG. 14 is a schematic diagram illustrating the preparation of a chemometric model based on 2D fluorescence spectra in continuously agitated microtiter plates by adding analytes of interest at different times during cultivation, FIG. 15 are graphs illustrating 2D fluorescence spectra recorded during cultivation of *Escherichia coli* in a minimal medium with an initial glucose concentration of 8 g $L^{-1}$ and an initial sorbitol concentration of 1.5 g $L^{-1}$ in a microtiter plate, FIG. 16 are graphs illustrating the course of the glucose, sorbitol and biomass concentrations and pH values of the cultivation according to FIG. 15.

FIG. 14 shows an alternative method for preparing chemometric models based on 2D fluorescence spectra. A plurality of cultivations with the same starting conditions are carried out in parallel in the microreactors of an agitated microtiter plate and monitored by recording of 2D fluorescence spectra. At different times, in the example shown in FIG. 14 after 3, 5, and 8 hours, an analyte is added to selected microreactors, resulting in known jumps in concentration. The result is that the reactions in the selected microreactors are no longer carried out under the same conditions. These modifications are detected by continuous recording of 2D fluorescence spectra in the microreactors of the microtiter plate. The effect of the defined modifications on the recorded 2D fluorescence spectra is used for developing chemometric models. However, the dilution effects resulting from the addition of water can also be used for developing chemometric models. The addition of water to the culture broth also causes concentration decreases that can be detected by means of the 2D fluorescence spectra.

For example, in addition to the concentrations of individual substances of the liquid cultures, the OTR can also be determined based on the recorded 2D fluorescence spectra using chemometric models. For the first time, therefore, the method according to the invention and the device for carrying out the method allow the oxygen transfer rate to be measured broken down according to individual microreactors of a microtiter plate based on 2D fluorescence spectra. Moreover, the pH can be determined by means of 2D fluorescence spectra in combination with chemometric models. The prior art for determination of pH is the use of optodes or dyes in microtiter plates. Optodes or dyes are not required for pH determination according to the present invention.

EXAMPLES

Figure 15:
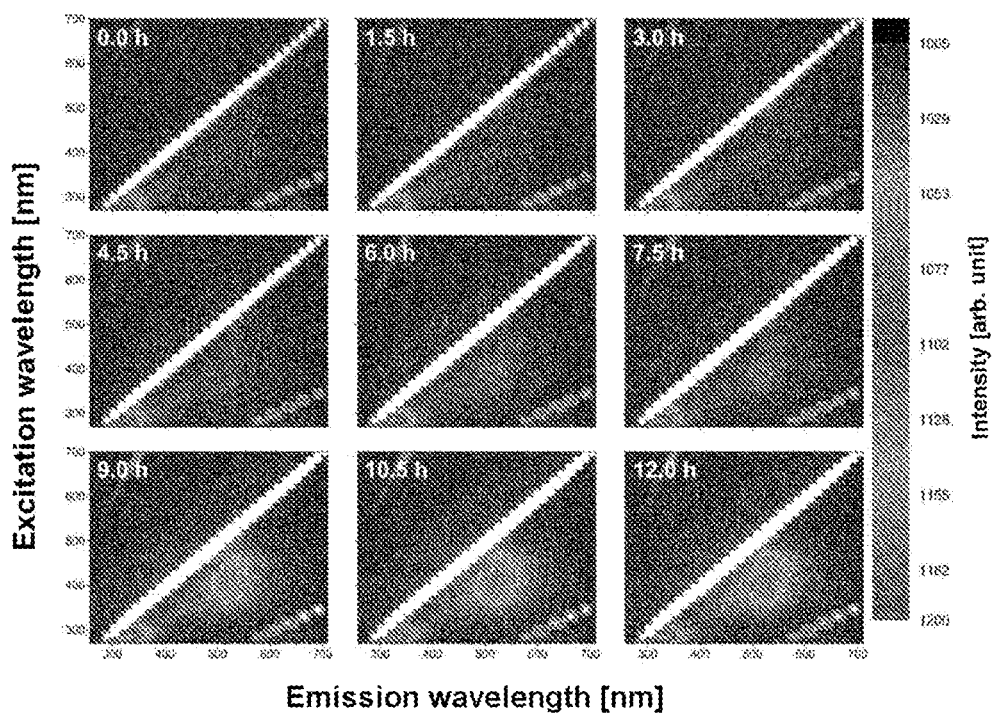

FIG. 15 shows 2D fluorescence spectra for cultivation of *Escherichia coli* in a minimal medium with an initial glucose concentration of 8 g $L^{-1}$ and an initial sorbitol concentration of 1.5 g $L^{-1}$.

Figure 16:
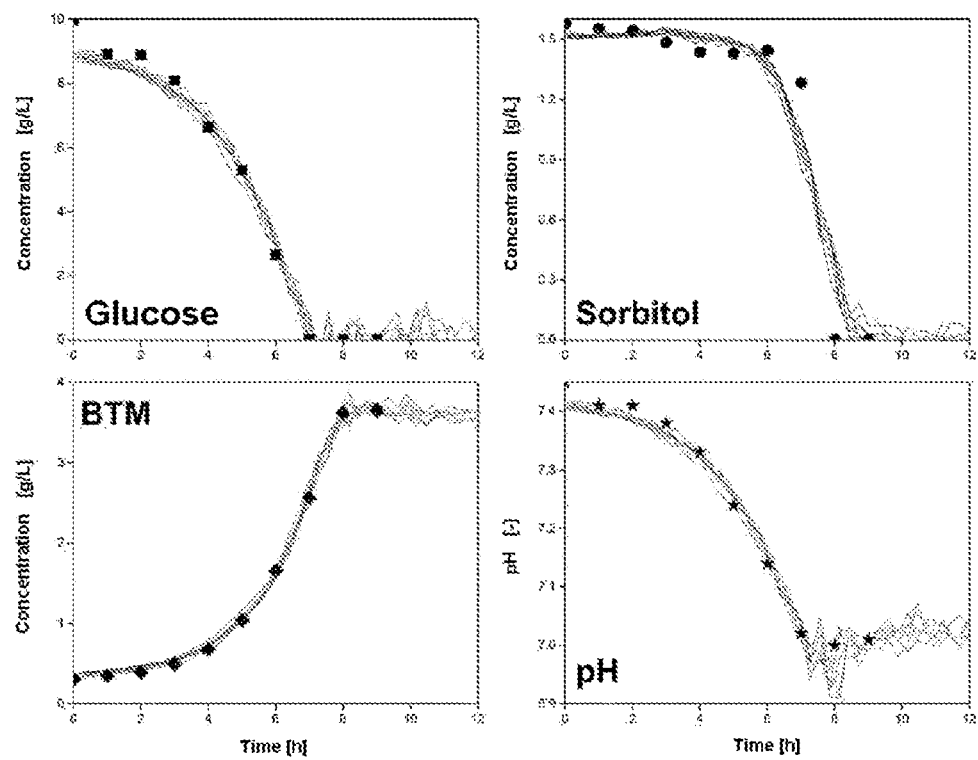

In addition to the increase in biogenic fluorescence (excitation: 350-500 nm/emission: 500-600 nm), one can clearly see an increase over time in the region of aromatic amino acids such as tryptophan and tyrosine (excitation: 270-320 nm/emission: 300-370 nm). Based on these 2D fluorescence spectra, chemometric models can be used to determine the course of different process parameters. As numerous wavelength pairs in fluorescence spectra naturally show a similar course, regression based on a partial least squares regression (PLSR) or a principal component analysis (PCA) is particularly useful in this case. Both methods make it possible to reduce the high number of wavelength pairs (30 excitation wavelengths 1,024 emission wavelengths=30,720 wavelength pairs per 2D fluorescence spectrum) to a significantly smaller number of significant linear combinations. As an example, FIG. 16 shows a PLSR for determining the course of glucose, sorbitol and biomass concentrations and the course of pH during cultivation. In each case, the dark, filled-in symbols indicate the concentration or pH determined offline. The solid lines were determined based on the 2D fluorescence spectra by means of chemometric models.

Cultivation was initiated in 15 wells in parallel under the same conditions. The entire liquid culture was removed from a well every hour in order to examine the samples by high-performance liquid chromatography (HPLC). This means that after one hour, the liquid culture was completely removed from a well so that 14 cultivations could be further carried out in parallel. After two hours, the entire liquid culture was removed from the next well, allowing the cultivation to continue undisturbed in 13 other wells. This process was repeated 10 times, with the result that 5 online signals were present at the end.

It can be clearly seen from the example shown that it is possible to monitor cultivations in continuously agitated microtiter plates with 2D fluorescence spectra. *E. coli* is one of the most rapidly growing microorganisms used in biotechnology. Even with this high growth rate, the system presented makes it possible to produce a sufficiently high data density to allow the course of various process-relevant concentrations and pH to be followed.

| Reference nos. | |
|---|---|
| No. | Name |
| 1. | Positioning unit |
| 2. | Microtiter plate |
| 2a. | Microreactors |
| 3. | Beam guidance system |
| 3a. | Optical waveguide (fluorescence measurement) |
| 3b. | Coupler |
| 3c. | Optical waveguide (backscattering) |
| 4. | Microreactor platform |
| 5. | Orbital shaker |
| 6. | Computer |
| 7. | Sensor matrix |
| 8. | Light source |
| 11. | Position sensor |
| 11a. | Hall effect sensor |
| 11b. | Magnet |
| 12. | Hall effect sensor |
| 13. | Optical element |
| 14. | Mechanical shutter |
| 15. | Monochromator |
| 16. | Emission spectrum |
| 17. | Liquid sickle |
| 18. | Measurement segment |
| 19. | Electromagnetic radiation (excitation light) |
| 20. | Screen |
| 21. | Collimator |
| 22. | Semitransparent mirror |
| 23. | Optical waveguide |

The invention claimed is:

1. A method for determining process parameters using 2D fluorescence spectroscopy in liquid cultures using a device having a plurality of microreactors of at least one microtiter plate, the liquid cultures being held in the microreactors, an orbital shaker configured to agitate the liquid cultures by moving the at least one microtiter plate in an agitating motion at least until completion of cultivation in all of the microreactors, and at least one measuring device configured to record 2D fluorescence spectra of the liquid cultures during the cultivation, the at least one measuring device being decoupled from the agitating motion of the microtiter plate, the method comprising the following steps:

1.1 producing monochromatic excitation light, an excitation wavelength of which is modified step by step so that the excitation light is produced with different excitation wavelengths, 1.2 successively introducing the excitation light with different excitation wavelengths into the liquid culture in one of the microreactors, 1.3 guiding emission spectra from the liquid culture in the one of the microreactors to an optical element that decomposes the emission spectrum for each excitation wavelength into the different individual wavelengths and depicts the emission spectrum fanned out on a sensor matrix of the at least one measuring device with photosensitive sensors to form bands on the sensor matrix for the individual wavelengths, 1.4 recording, using the sensor matrix of the at least one measuring device, a 2D fluorescence spectrum by measuring an intensity of the different individual wavelengths of each emission spectrum for each excitation wavelength successively introduced in the liquid culture in the one of the microreactors, and 1.5 using steps 1.1-1.4 to record 2D fluorescence spectra of the liquid cultures in further microreactors of the at least one microtiter plate, wherein the step of guiding includes selectively modifying a position of the optical element so that a region of the emission spectrum having a wavelength less than or equal to the excitation wavelength is guided past the sensor matrix.

2. The method according to claim 1, wherein the step of introducing the excitation light and the step of guiding the emission spectra are carried out through a surface on the underside of each microreactor that is transparent for the excitation light and the emission spectra.

3. The method according to claim 1, wherein the excitation light is generated by an automatically tunable monochromator for spectral isolation of different wavelengths from the incident light of a light source.

4. The method according to claim 3, wherein the step of introducing the excitation light from the monochromator to the liquid culture and the step of guiding the emission spectrum from the liquid culture to the optical element are carried out by a beam guidance system comprising an optical coupler, wherein the optical coupler for introducing the excitation light into the liquid culture and for coupling the emission spectrum into the beam guidance system is oriented with respect to the microreactor containing the liquid culture.

5. The method according to claim 4, wherein the optical coupler is not moved during recording of the 2D fluorescence spectrum, so that the agitated microreactors move relative to the optical coupler.

6. The method according to claim 4, wherein the optical coupler, following the step of recording of the 2D fluorescence spectrum, is moved by a positioning unit between the microreactors of the at least one microtiter plate.

7. The method according to claim 4, wherein an agitation diameter of the orbital shaker is adjusted in such a way that at least two microreactors of the plurality of microreactors, during one rotation of the orbital shaker, successively circle above the optical coupler of a measuring device of the at least one measuring device, and the recorded fluorescence spectra are assigned to the at least two microreactors circling above the optical coupler.

8. The method according to claim 4, wherein the excitation light and the emission spectrum in the beam guidance system are transferred via separate optical waveguides or a y-shaped optical waveguide with separate fibers for the excitation light and the emission spectrum.

9. The method according to claim 4, wherein in the beam guidance system, the excitation light is deflected by a semitransparent mirror and introduced into the liquid culture via an optical waveguide with only one fiber, and the emission spectrum is transferred through the optical waveguide and the semitransparent mirror to the optical element.

10. The method according to claim 3, wherein an agitation diameter of the orbital shaker is adjusted in such a way that the excitation light during recording of the fluorescence spectrum is introduced exclusively into the liquid culture of one of the microreactors and the emission spectrum of this liquid culture is exclusively introduced into the optical coupler.

11. The method according to claim 1, wherein the at least one measuring device includes a plurality of measuring devices and the 2D fluorescence spectra of the liquid cultures in different microreactors are recorded simultaneously by the plurality of measuring devices.

12. The method according to claim 11, the step of introducing the excitation light from the monochromator to the liquid culture and the step of guiding the emission spectrum from the liquid culture to the optical element are carried out by a beam guidance system comprising a plurality of optical couplers corresponding to the plurality of measuring devices, wherein the plurality of optical couplers of the plurality of measuring devices are movable by a common positioning unit between the microreactors of the at least one microtiter plate.

13. The method according to claim 1, wherein the step of introducing the excitation light is interrupted depending on the position of the orbital shaker.

14. The method according to claim 13, wherein the position of the orbital shaker is determined by a position sensor.

15. The method according to claim 1, wherein the region of the emission spectrum having the wavelength less than or equal to the excitation wavelength is excluded from the measurement of the emission spectrum.

16. The method according to claim 1, further comprising the step of at least one of:
collimating or focusing the excitation light before the step of introducing, and
concentrating the emission spectrum.

17. The method according to claim 1, further comprising the step of measuring backscattering of the excitation light irradiated into the liquid culture using a separate photosensitive sensor of the measuring device.

18. The method according to claim 1, wherein the device includes a pipetting robot and the method further includes at least one of:
during cultivation, automatically taking samples of the liquid culture from one of the microreactors at different times by the pipetting robot and analyzing the samples offline with respect to specified process parameters of the process parameters, and
automatically adding at least one of substances and liquids to the liquid culture at different times by the pipetting robot.

19. The method according to claim 18, wherein the process parameters of the samples analyzed offline and the 2D fluorescence spectra recorded at the different sampling times are used to prepare chemometric models.

20. The method according to claim 19, wherein at least one process parameter is determined using a 2D fluorescence spectrum recorded from a liquid culture using the chemometric models.

21. The method according to claim 1, wherein
in the plurality of microreactors, cultivations of liquid cultures are carried out under the same conditions, in each of the above-mentioned liquid cultures, 2D fluorescence spectra are recorded offset in time, and
the respective 2D fluorescence spectra recorded offset in time in the plurality of microreactors are brought together in such a way that the fluorescence spectra from the above-mentioned microreactors are measured over a time vector.

22. The method according to claim 1, wherein cultivations in the liquid cultures are carried out in the plurality of microreactors under the same conditions, wherein initial values of the process parameters to be measured in the liquid cultures in the microreactors are different, and the effect of the different initial values on the recorded 2D fluorescence spectra is used to develop chemometric models.

23. The method according to claim 1, wherein cultivations in the liquid cultures are carried out in the plurality of microreactors under the same conditions, wherein at different times, at least one of a substance and a liquid is added to individual microreactors of the plurality of microreactors, said at least one of a substance and a liquid modifying the process parameter to be measured in the liquid cultures in a defined manner, and the effect of the modifying on the recorded 2D fluorescence spectra is used to develop chemometric models.

24. The method according to claim 1, wherein:
a functional relationship on which the modification of a process parameter in one of the liquid cultures is based is described by a mechanistic/mathematical model,
model parameters for the mathematical model are assumed at the beginning of the cultivation,
the process parameters determined based on the mathematical model are compared with the 2D fluorescence spectra recorded at different times during cultivation of this liquid culture, and
the model parameters are corrected depending on the comparison.

25. A device for measuring process parameters using 2D fluorescence spectroscopy, comprising:
a microreactor platform connected to an orbital shaker on which at least one microtiter plate with a plurality of microreactors is arranged, the microreactors configured to hold liquid cultures and the orbital shaker configured to agitate the liquid cultures by moving the at least one microtiter plate in an agitating motion,
a light source,
an automatically tunable monochromator for spectral isolation of different wavelengths from the incident light of the light source, configured to produce monochromatic excitation light, an excitation wavelength of which is modified step by step so that the excitation light is produced with different excitation wavelengths,
a beam guidance system comprising an optical coupler that is configured for transferring the excitation light from the monochromator to the liquid culture and for transferring the emission spectrum from the liquid culture to an optical element,
wherein the optical coupler for introducing the excitation light into the liquid culture and for coupling the emission spectrum into the beam guidance system is oriented with respect to a section of the microreactor that is permeable to electromagnetic radiation and
wherein the optical element decomposes the emission spectrum for each excitation wavelength into the different individual wavelengths and fans out the individual wavelengths, and
a sensor matrix with photosensitive sensors, the optical element depicting the fanned-out individual wavelengths across the sensor matrix to form bands on the sensor matrix for the individual wavelengths, wherein the sensor matrix is configured to record a 2D fluorescence spectrum by measuring the intensity of the different individual wavelengths for each emission spectrum, and wherein a position of the optical element is modifiable so that a region of the emission spectrum having a wavelength less than or equal to the excitation wavelength is guided past the sensor matrix.

26. The device according to claim 25, further comprising a positioning unit configured to move the optical coupler between the microreactors of the at least one microtiter plate.

27. The device according to claim 25, wherein
the at least one measuring device comprises a plurality of measuring devices that each comprise a light source, an automatically tunable monochromator, a beam guidance system, an optical element and a sensor matrix,
the 2D fluorescence spectra of the liquid cultures in different microreactors being measured at the same time by the plurality of measuring devices.

28. The device according to claim 27, wherein the optical couplers of the plurality of measuring devices are moveable between the microreactors of the at least one microtiter plate by a common positioning unit.

29. The device according to claim 25, further comprising a shutter arranged in the optical path of the excitation light that is configured to interrupt the excitation light depending on the position of the orbital shaker.

30. The device according to claim 29, further comprising a position sensor for measuring the position of the orbital shaker arranged on the orbital shaker and a controller configured for processing the measured position signals of the position sensor and for interrupting the excitation light by the shutter depending on the position signal.

31. The device according to claim 25, further comprising a lens for collimation or focusing of the excitation light arranged on the coupler.

32. The device according to claim 25, wherein the at least one measuring device comprises a photosensitive sensor that is configured to measure the backscattering of the excitation light irradiated into the liquid culture.

33. The device according to claim 25, wherein the beam guidance system comprises separate optical waveguides or a y-shaped optical waveguide with separate fibers.

34. The device according to claim 25, wherein the beam guidance system comprises a semitransparent mirror and an optical waveguide with only one fiber as optical components, wherein the optical components are arranged relative to each other in such a way that the excitation light is deflected by the semitransparent mirror and introduced via the optical waveguide into the microbial liquid culture, and the emission spectrum is transferred through the optical waveguide and the semitransparent mirror to the optical element.

35. The device according to claim 25, further comprising a pipetting robot configured to at least one of automatically take samples of the microbial liquid culture from a microreactor and add liquids at different times during cultivation.

* * * * *